US011357940B2

(12) United States Patent
Rapoport (10) Patent No.: US 11,357,940 B2
(45) Date of Patent: Jun. 14, 2022

(54) METHOD AND APPARATUS FOR BREATHING ASSISTANCE

(71) Applicant: Ninox Medical Ltd., Jerusalem (IL)

(72) Inventor: Alex Rapoport, Rishon le Zion (IL)

(73) Assignee: KEEPMED LTD., Rishon le Zion (IL)

( * ) Notice: Subject to any disclaimer, the term of this patent is extended or adjusted under 35 U.S.C. 154(b) by 1266 days.

(21) Appl. No.: 14/382,322

(22) PCT Filed: Mar. 4, 2013

(86) PCT No.: PCT/IL2013/050192
§ 371 (c)(1),
(2) Date: Sep. 1, 2014

(87) PCT Pub. No.: WO2013/132483
PCT Pub. Date: Sep. 12, 2013

(65) Prior Publication Data
US 2015/0128948 A1 May 14, 2015

Related U.S. Application Data

(60) Provisional application No. 61/606,531, filed on Mar. 5, 2012.

(51) Int. Cl.
*A61M 16/00* (2006.01)
*A61M 16/20* (2006.01)
*A61M 16/08* (2006.01)
*A61M 16/06* (2006.01)

(52) U.S. Cl.
CPC .... *A61M 16/0069* (2014.02); *A61M 16/0003* (2014.02); *A61M 16/0616* (2014.02);
(Continued)

(58) Field of Classification Search
CPC .......... A61M 16/0069; A61M 16/0866; A61M 16/201; A61M 16/0616; A61M 16/0003;
(Continued)

(56) References Cited

U.S. PATENT DOCUMENTS 3,905,362 A * 9/1975 Eyrick .............. A61M 16/0012
128/202.22
4,655,213 A 4/1987 Rapoport et al.
(Continued)

FOREIGN PATENT DOCUMENTS

JP 2006507873 A 3/2006
WO 9639206 A2 12/1996
(Continued)

OTHER PUBLICATIONS

Beyond the Basics: Interpreting Vital Signs, Dec. 1, 2006 (Year: 2006).*
(Continued)

*Primary Examiner* — Victoria Murphy
(74) *Attorney, Agent, or Firm* — Mark M. Friedman (57) ABSTRACT

Methods and system for treating obstructive sleep apnea and snoring are disclosed. The system generally comprises a mask for delivering pressurized air to patient's breathing orifice, a sensing mechanism for continuously assessing the state of patient's breathing and a pressure generator for generating the pressurized air in the mask. The pressurized air is applied to the breathing orifice only during selected portions of the breathing cycle, when such pressure might be required to prevent occlusion of the airway or to restore patency of the airway after such occlusion occurs.

6 Claims, 7 Drawing Sheets

(52) U.S. Cl.
CPC .... *A61M 16/0666* (2013.01); *A61M 16/0694* (2014.02); *A61M 16/0866* (2014.02); *A61M 16/201* (2014.02); *A61M 16/205* (2014.02); *A61M 16/0057* (2013.01); *A61M 16/0063* (2014.02); *A61M 16/024* (2017.08); *A61M 16/0683* (2013.01); *A61M 16/208* (2013.01); *A61M 2016/003* (2013.01); *A61M 2016/0021* (2013.01); *A61M 2016/0027* (2013.01); *A61M 2016/0033* (2013.01); *A61M 2205/3334* (2013.01); *A61M 2205/3375* (2013.01); *A61M 2205/35* (2013.01); *A61M 2205/52* (2013.01); *A61M 2205/8206* (2013.01); *A61M 2206/10* (2013.01); *A61M 2230/42* (2013.01)

(58) Field of Classification Search
CPC ............ A61M 16/0694; A61M 16/205; A61M 16/20; A61M 16/0063; A61M 2206/10; A61M 2205/3334; A61M 2205/52; A61M 2205/35; A61M 2230/42; A61M 2205/8206; A61M 2016/003
See application file for complete search history.

(56) References Cited

U.S. PATENT DOCUMENTS

| | | | | |
|---|---|---|---|---|
| 5,237,987 | A | * | 8/1993 | Anderson ........... A61M 16/024 128/204.18 |
| 6,131,571 | A | * | 10/2000 | Lampotang ........... A61M 16/00 128/204.18 |
| 2002/0014240 | A1 | | 2/2002 | Truschel et al. |
| 2003/0121519 | A1 | | 7/2003 | Estes et al. |
| 2004/0187870 | A1 | | 9/2004 | Matthews et al. |
| 2004/0255943 | A1 | | 12/2004 | Morris et al. |
| 2005/0020932 | A1 | | 1/2005 | Haberland et al. |
| 2006/0070624 | A1 | | 4/2006 | Kane et al. |
| 2007/0295338 | A1 | | 12/2007 | Loomas et al. |

FOREIGN PATENT DOCUMENTS

| | | |
|---|---|---|
| WO | WO96/39206 A2 | 12/1996 |
| WO | 2010076711 A1 | 7/2010 |
| WO | 2011029074 A1 | 3/2011 |
| WO | 2012001621 A1 | 1/2012 |
| WO | 2012006339 A2 | 1/2012 |
| WO | WO2012/001621 A1 | 1/2012 |

OTHER PUBLICATIONS

Office Action dated Oct. 24, 2016, in corresponding Chinese Patent Application No. 2013800235937.
PCT International Search Report and Written Opinion of the ISA, dated Jun. 25, 2013 in PCT/IL13/050192.
Extended European Supplementary Search Report of the European Patent Office, in corresponding European patent application No. 13757119.6, dated Aug. 17, 2015.

* cited by examiner

METHOD AND APPARATUS FOR BREATHING ASSISTANCE

FIELD OF THE INVENTION

The present invention relates to the field of the application of positive pressure to patients airway for treatment of Obstructive Sleep Apnea.

BACKGROUND OF THE INVENTION

Obstructive sleep apnea (OSA) is an increasingly prevalent condition in modern society. OSA is characterized by repetitive episodes of complete (apnea) or partial (hypopnea) upper airway obstruction occurring during sleep. Available evidence indicates that pharyngeal collapse is responsible for the recurrent upper airway (UA) obstruction during sleep in patients with OSA. Apnea episodes (cessation of airflow) lasting 10 seconds or longer are considered clinically significant. Apnea episodes are usually approximately 20-40 seconds and rarely last several minutes.

Continuous positive airway pressure (CPAP) is the standard treatment option for obstructive sleep apnea. One previous device and method for the treatment of sleep apnea is described in U.S. Pat. No. 4,655,213 to Rapoport in which continuous positive air pressure (CPAP) is applied to the patient's airway.

Continuous positive pressure is applied to the upper airway with a nasal mask, nasal pillow, nasal prong, oral mask, hybrid oronasal mask, full face and total face mask. Throughout this specification the reference to mask is intended to incorporate a reference to any one of, or combinations of, these masks.

A standard CPAP device consists of a blower unit that produces positive-pressure airflow. This airflow is usually applied at the nose through a flexible tube and is then directed through a sealed mask to the upper airway. CPAP acts as a pneumatic splint to maintain airway patency during sleep. The pressure needed is typically 4-20 cm of water.

A variation of CPAP, is BiPAP that permits independent adjustment of the pressures delivered during inspiration and expiration. Another variation of CPAP is the Automatic Positive Airway Pressure (APAP) device that adjusts the blow automatically to achieve the minimum pressure needed to keep the airway open during sleep. Most devices use complex algorithms to adjust pressure after an event (an apnea, hypopnea, or snore) has occurred by monitoring the users inspiratory flow-time curve. Changes in this curve indicate the likely occurrence of an apnea, hypopnea, or snore. Throughout this specification the reference to CPAP is intended to incorporate a reference to any one of, or combinations of, these forms of pressure delivery.

In conventional CPAP systems, the air is supplied to the mask by an air flow generator typically placed in proximity to the patient's bed. The air flow generator produces the required pressure in patient/s mask by blowing an airflow typically ranging between 20 l/min and 170 l/min, but usually between 60 l/min and 120 l/min. A large diameter air delivery tube is needed for the delivery of the air generated by the air flow generator to the mask. The masks used in CPAP treatment generally include a vent for washout of the gas to atmosphere. The vent is normally located in the mask or in the gas delivery conduit adjacent the mask. Most of the airflow escapes through the exhaust port or otherwise leaks out, because typically, the patient needs only between 6 l/min and 12 l/min of breathing air. Typically, conventional CPAP systems control the pressure by changing the airflow produced by the blower.

In conventional systems, the high airflow delivered to the patient creates many undesirable side effects. The tube restricts the movement of the patient, creates a "tubing drag" that may cause leaks between the mask seal and the patient's face and/or discomfort. Additionally, the length of the tube may impart a lag in the response in delivering pressured air from the air flow generator to the mask. Furthermore, increased flow impedance and/or pressure drop due to diameter and length of tubing may also necessitate a larger blower motor to compensate for the pressure drop along the air delivery tube.

High airflow-related complications include a sensation of suffocation or claustrophobia, difficulty exhaling, inability to sleep, musculoskeletal chest discomfort, aerophagia, sinus discomfort and conjunctivitis (due to air leaks). Additionally, air swallowing is a common problem.

In many patients, the airflow causes nasal and/or oral dryness, rhinorrhea, nasal congestion and frequent nosebleeds. Although using a humidifier might provide some remedy, but the humidifier itself creates new problems such as droplet formation inside the tubing (rainout) that may drain into the face mask and be quite uncomfortable. The distilled water used in CPAP humidifiers may grow organisms and become foul-smelling.

It is estimated, that more than half of the patients fail to comply with the prescribed CPAP therapy because of the inconvenience and the side effects of the existing methods.

It would therefore be desirable and advantageous to devise an effective method and apparatus for treatment of OSA, while eliminating the need for high flow blower and the tube.

Accordingly, it is an object of the present invention to overcome the disadvantages of prior art methods and provide an improved method and apparatus for treatment of OSA and other disorders that involve occluded air ways. More specifically, it is an object of the invention to provide an apparatus for preventing upper airway occlusion and for restoring the patency of the airway by low-flow, pressurized air.

Another objective is simplifying the CPAP system and minimizing size of the system.

The foregoing objectives are attained by the apparatus and method of the present invention.

The disclosures of each of the publications mentioned in this section and in other sections of the specification, are hereby incorporated by reference, each in its entirety.

SUMMARY OF THE INVENTION

The present invention seeks to provide method and a system for treating OSA and snoring by preventing occlusion of the upper airway of a subject and for restoring the patency of occluded airway, if such occlusion occurs. Such goals may be achieved by providing pressurized air to patient's breathing orifice, only during a portion of the breathing cycle, when such pressure might be required to prevent occlusion of the airway or to restore patency of the airway after such occlusion occurs. During the time when such pressurized air is not required, the system may allow spontaneous breathing of non-pressurized atmospheric air.

The system may generally comprise a mask for delivering pressurized air to patient's Breathing Orifice, a sensing mechanism for continuously assessing the state of patient's breathing and a pressure generator for generating the pressurized air in the mask.

The system may apply pressurized air to the Breathing Orifice only during selected portion of the expiration cycle. Such pressurized air may cause an increase of the upper airway caliber thus preventing a potential pharyngeal collapse, which is typically the cause of occlusion of the upper airway.

The system may generate such pressurized air in the mask by selectively restricting the expiration air flow through the exhaust valve of the mask. The level of the generated air pressure and the timing of its initiation and termination may be dynamically selected to match the individual patient's needs.

The pressurized air may be generated and accumulated by the pressure generator until such pressurized air may be controllably released into the mask, thus elevating the pressure within the mask.

The patient may be breathing spontaneously as long as the airway is not occluded. When the occlusion occurs, pressurized air may be provided to patient's upper airway, thus removing the obstruction and stimulating restoring of the patency of the airway.

To make the use of the system more comfortable, the system may be set to soft-start operating only after the patient enters a sleeping phase in which apnea events my occur. The time to such entry may be estimated using data generally known in the art. The system may also detect such entry by sensing the occurrence of apnea events.

Additional aspects of the present invention may include apparatus adapted to record the breathing patterns, apnea events, utilization history, and remote reporting and additional functions typically existing in modern CPAP systems.

The method and apparatus of the present invention broadly may be used for treating OSA, snoring and other medical conditions that may involve occlusion of the airway as well as continuous monitoring of the breathing status The method may further comprise providing means for spontaneous breathing of non-pressurized atmospheric air.

The method may comprise providing pressurized air to patient's Breathing Orifice selectively only during predetermined portion of the breathing cycle.

The method may further comprise providing pressurized air to patient's Breathing Orifice during a portion of the expiration phase of the breathing cycle for increasing the upper airway caliber and thus preventing the occlusion of the upper airway during the following inspiration phase of the breathing cycle.

The method may further comprise applying the pressurized air to the upper airway only if the inspiration attempt does not lead to successful inhaling within a predetermined period of time. The method may further comprise increasing the pressure in the occluded upper airway until patency is restored and triggering the pharyngeal dilator reflex that may prevent the collapsing of the upper airway.

The method may further comprise generating and accumulating the pressurized air during the time when the patient breathes spontaneously and, providing the accumulated pressurized air to patient's upper airway when an occlusion occurs thus removing the obstruction and restoring the patency of the upper airway.

The method may further comprise allowing spontaneous breathing until the patient enters a sleeping phase in which apnea events may occur and selectively applying pressurized air afterwards.

The method may further comprise providing pressurized air by controllably (completely or partially) restricting the escape of exhaled airflow from the mask through the exhaust.

The method may further comprise providing pressurized air from external source such as pressure generator or pressurized air container or alike.

Throughout this specification it is to be understood that:
1. The reference to air is meant to include any breathable gas.
2. The reference to Breathing Orifice is meant to include either the nostrils or the mouth or the nostrils and the mouth combined.
3. The reference to spontaneous breathing means breathing of non-pressurized or ambient air.
4. Zero pressure means ambient atmospheric pressure.

The Invention Offers Numerous Advantages Over Existing Systems for Treating OSA:

The present invention may allow using very low average airflow for producing the required pressure. Such low airflow may eliminate the high-airflow related side effect of the existing systems such as:

sensation of suffocation or claustrophobia, difficulty exhaling, inability to sleep, musculoskeletal chest discomfort, aerophagia, sinus discomfort, conjunctivitis and air swallowing, nasal and/or oral dryness, rhinorrhea, nasal congestion and frequent nosebleeds and inconvenience of the noise created by the high airflow.

The low airflow may not require the use of humidifier, thus reducing the cost and avoiding the side effected related to humidifiers such as the rainout.

A very small and lightweight pressure generator may be used instead of bulky and possibly noisy blowers that are typical to the conventional systems. Such pressure generator may be conveniently integrated into the mask or into the headgear, thus avoiding the drawback associated with tubing. Such drawbacks which are typical to conventional systems include restricted movement of the patient, "tubing drag", lag in the response in delivering pressured air from the air flow generator to the mask, etc.

Additional advantage is that during part of the expiration phase, the pressure may be made lower than with the existing systems making the expiration more comfortable and reducing the build-up of the $CO_2$ and humidity in the system.

Another advantage is that the system may be set to intervene the spontaneous breathing only during the time the patient is in the sleeping phase that is characterized by apnea events.

Still another advantage is that the system in accordance to present invention may be simpler, more convenient and less expensive than the alternative solutions.

BRIEF DESCRIPTION OF DRAWINGS

The foregoing and other objects, features and advantages of the invention will become apparent from the following more particular description of preferred embodiments of the invention, as illustrated in the accompanying drawings. The drawings are not necessarily to scale, emphasis instead being placed on illustrating the principles of the present invention.

DETAILED DESCRIPTION OF PREFERRED EMBODIMENTS

The present invention seeks to provide a system for preventing of occlusion of patient's airway. The present invention further seeks to provide a system for restoring the patency of the airway when such airway becomes occluded. According to the principles of present inventions, those goals may be achieved by creating a Temporary Elevated Pressure (TEP) in patient's upper airway only during a particular portion of the expiration phase of patient's breathing cycle or/and by introducing a short surge of pressurized air when the occlusion is detected. The rest of the time, the patient may be set to spontaneously breathe ambient air at atmospheric pressure.

TEP Applied During Portion of Expiration

The TEP may be generated by mechanically restricting the patient's own expiration air flow thus causing pressure elevation in the upper airway. The TEP may be generated during a specific portion of the expiration phase for example, after the peak in the exhaled airflow or during the End of Expiration Segment (EES) of the breathing cycle.

The TEP may be generated by applying a short surge of pressurized air to the patient's Breathing Orifice when the upper airway becomes occluded, but before such occlusion becomes clinically significant.

In one embodiment, the TEP may be provided only during sleep. For example, a delay may be provided to enable the patient to breathe spontaneously ambient air, until the patient falls asleep or until the patient enters a sleep phase that is characterized by apnea events.

Figure 1:
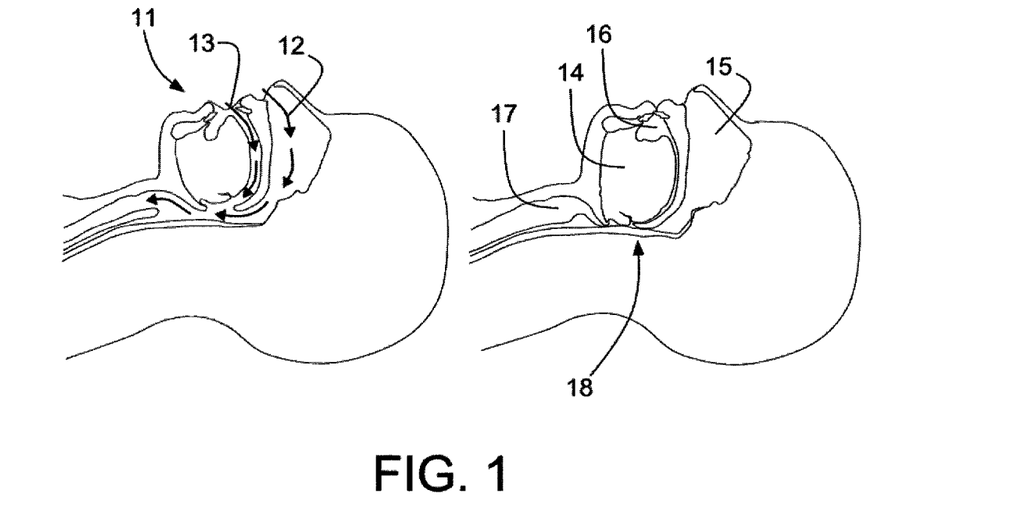
FIG. 1 is a general view upper airway anatomy during normal breathing and when the upper airway is occluded.

Reference is now made to FIG. 1 which illustrates a normal nasal breathing air path 12 and an oral breathing air path 13. During the apnea episode, a nasal cavity 15 and an oral cavity 16 are isolated from a trachea 17 by a collapsed tissue such as tongue 14 that creates an occlusion 18.

Figure 2A:
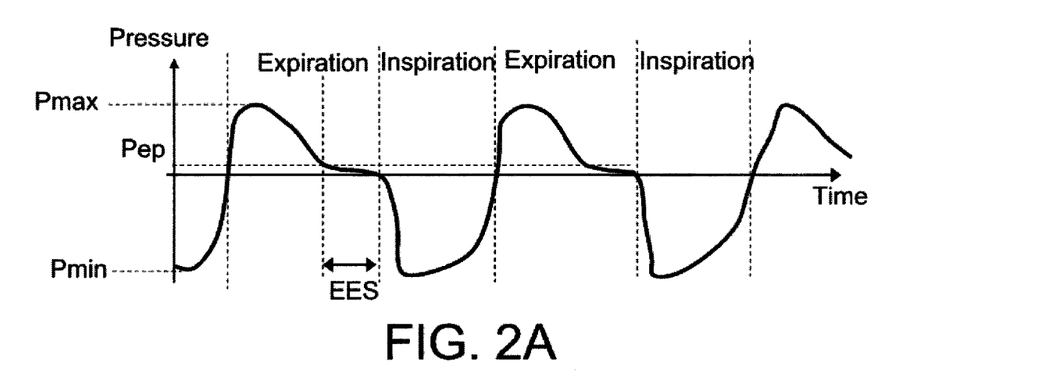
FIG. 2A is an illustration an upper airway pressure waveform of a spontaneously and normally breathing subject.

Reference is now made to FIG. 2A which illustrates an example of a waveform of the air pressure P1 in the patient's nasal mask during normal, spontaneous nasal breathing. During spontaneous expiration, the pressure rises sharply to its maximum value Pmax and gradually reduce to the atmospheric pressure. The End of Expiration Segment is defined as a time from a point when most of the tidal air volume has been expelled out of the lungs and until the onset of the following inspiration attempt. When inspiration starts, the pressure drops sharply to Pmin and then rises gradually back to the atmospheric pressure.

It is believed that the occlusion typically occurs during the EES, while the onset of inspiration produces a sharp negative pressure that may also trigger a complete occlusion of the airway.

Figure 2B:
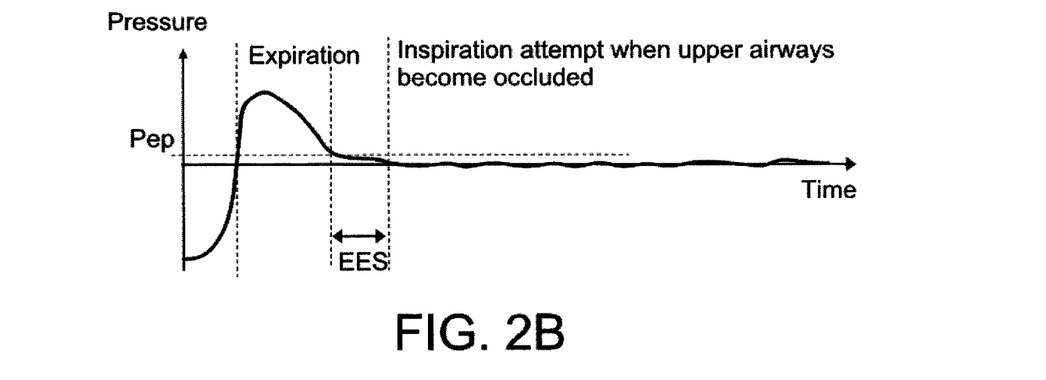
FIG. 2B is an illustration an upper airway pressure waveform of a spontaneously breathing subject above upper airway occlusion, when such occlusion occurs.

FIG. 2B is an exemplary illustration an upper airway pressure waveform of an air pressure P1 in the patient's nasal mask of a spontaneously breathing subject, when a total occlusion of the upper airway occurs. At the end of the EES, when the subject makes an inspiration attempt, the pressure above the occlusion remains close to zero.

Figure 2C:
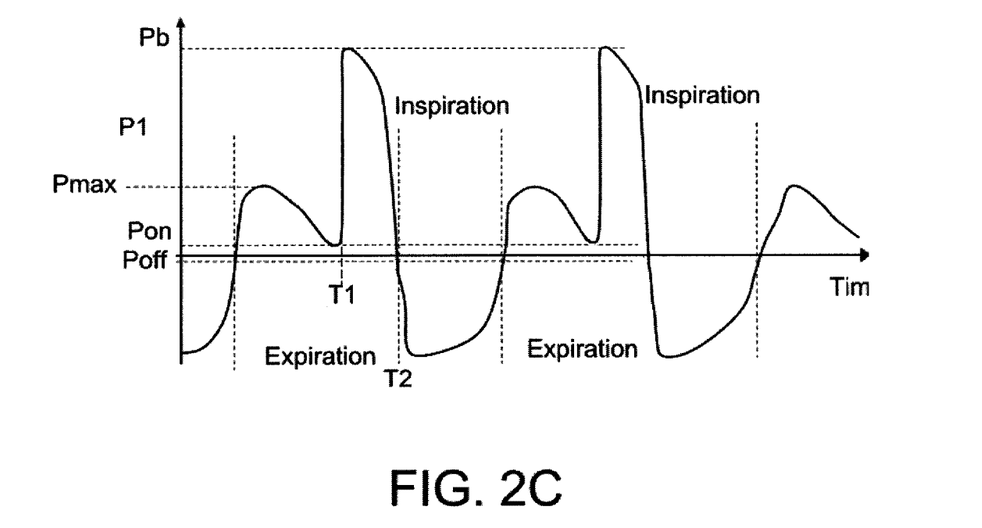
FIG. 2C is an illustration of an example of a pressure waveform within subject's mask modified operational according to the principles of present invention.

FIG. 2C illustrates an example of a waveform of an air pressure in patient's nasal cavity modified by introducing the TEP between the time T1 and the time T2, which approximately corresponds to the EES segment of the breathing cycle. The maximum pressure of the TEP is Pb. The parameters T1, T2 and Pb are selected such that the generated TEP preserves the patency of the airway while being well tolerated by the patient.

Figure 2D:
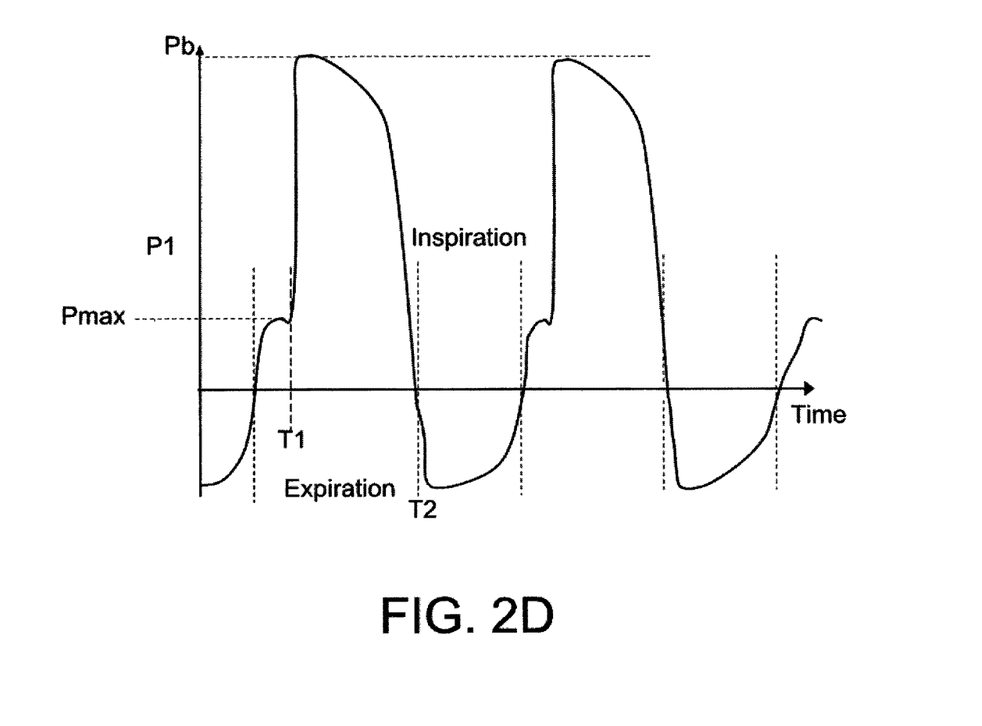
FIG. 2D is an illustration of another example of a pressure waveform within subject's mask operational according to the principles of present invention.

The value of the time point T1 may be set as a time after one or more characteristic reference points of the breathing cycle curve. For example, as shown in FIG. 2D, such a reference point may be a zero crossing that manifests the beginning of expiration. Another reference point may be the peak expiration pressure. Additionally, T1 may be set as a point when the declining pressure reaches a certain value relatively to Pmax. For example, T1 may be selected shortly after Pmax while the T2 may be selected when P1 drops to zero as illustrated in FIG. 2D.

The detection of the reference points may be based on pressure curves as well as air flow, temperature or any other parameter representative of the patient's breathing cycle. For example, such a parameter may be the pressure P1.

Generally, the pressure P1 is dependent of the patient's exhalation airflow and level flow restriction. A desired TEP is generated in a controllable manner by selectively restricting the patient's expiration air flow. The timing of beginning (T1) when P1=Pon and ending (T2) when P1=Poff of such restriction as well as the intensity of restriction applied, affects the maximum pressure Pb. Those parameters may be dynamically adjusted for optimal prevention of apnea events with minimum discomfort to the patient.

The optimal values of the Pb, T1 and T2 for preventing apneas are individual for every patient. Moreover, for the same patient, the optimal parameters may vary from night to night and even during the night. Typically, the TEP may be controlled such that the upper airway occlusion is prevented by automatically and dynamically matching the values Pb, T1 and T2 to each individual patient, with minimum discomfort to the patient. Typically, the exhalation airflow is highest at the beginning of the expiration phase. Therefore, the earlier in the expiration phase the flow restriction starts the higher is the pressure Pb. The Pb may also be controlled by the duration (T2-T1) of the restriction and by the intensity of the restriction applied.

The parameters T1, T2 and the intensity of restriction may be dynamically selected using a predetermined algorithm. For example, the pressure Pb may be gradually increased in each subsequent breath cycle or periodically, until an optimal value Pb at which the frequency of apneas is minimal. In addition to the maximum pressure Pb, the average pressure during of the TEP as well as the duration of the TEP and other characteristics of the TEP may also be dynamically adjusted until the frequency of apneas is reduced to minimum. The pressure function during TEP period may be made increasing, decreasing, fluctuating or any other form.

TEP Applied when the Upper Airway Become Occluded

The occlusion in the upper airway may be detected by monitoring of the breathing parameters such as pressure, flow, temperature, oxygen saturation, movement and/or other parameters. For example, one of such breathing parameters is the pressure P1. When the occlusion is detected and preferably before such occlusion persists long enough to become clinically significant, a surge of pressurized air is introduced to the upper airway and elevates the pressure in the upper airway to a level sufficient to temporary remove the occlusion. The resulting onset of airflow along the pharyngeal sensors should trigger the pharyngeal dilator reflex. The reflex should activate the pharyngeal dilator muscles that keeps the upper airway from collapsing as long as the inspiration (negative pressure) and the airflow persist. In other words, with the occlusion temporarily removed, the dilator muscles stimulated by the airflow are intended to maintain the patency of the upper airway, so the inspiration phase may be completed.

Figure 3:
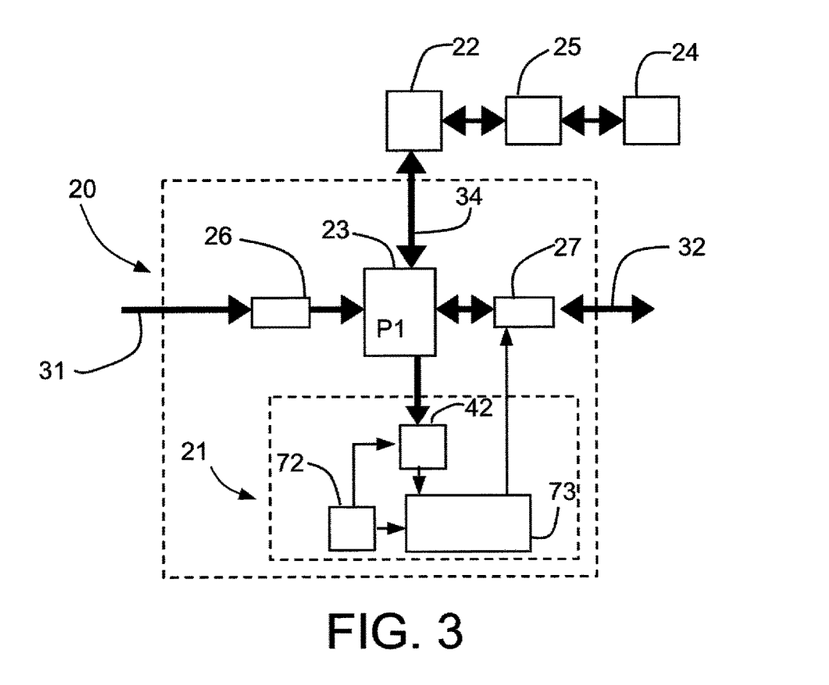
FIG. 3 is a schematic diagram of one embodiment incorporating the principles of present invention.

FIG. 3 is a block diagram of an exemplary system 20 that may be used for practicing the present invention. The system 20 is connected to a cavity 22 that represents the nasal cavity 15 or the oral cavity 16 of FIG. 1, or both those cavities combined. The cavity 22 is connected through a trachea 25 to the lungs 24.

The system 20 includes a mask 23 sealably and removably connected to the cavity 22 and allowing the airflow 34 between the cavity 22 and the mask 23. The mask 23 has an opening to allow airflow 32 to the atmosphere controlled by an adjustable valve 27. The system 20 further includes a pressure generator unit 21 connected to the mask 23. The pressure generator unit 21 comprises a sensor 42. The sensor 42 may be a pressure sensor for measuring the pressure within the mask 23, or may be acoustic sensors or flow sensors or other types of sensors or any combination thereof that are capable of detecting data that is indicative to the stage of the breathing cycle and to the patency of the airway. The mask 23 may have a second opening to the atmosphere controlled by a valve 26. The valve 26 is an optional addition, which is not essential.

The pressure generator unit 21 further includes a controller 73 for receiving and analyzing the data from the sensor 42 and for controlling the valve 27. Throughout this specification the reference to the controller is intended to incorporate a reference to a computer or logic components inclusive of any peripheral components such as power supply, memory components, A/D converters, amplifiers, drivers, wire/wireless communication components, electro-mechanical components such as solenoid valves, motors, pumps etc., known in the art for accomplishing the necessary function in accordance with the present invention.

The pressure generator unit may 21 further includes a power source 72 connected to the active components.

The valve 26 is a one-way valve that may be open when the pressure P1 in the mask 23 is lower than the atmospheric pressure outside the mask 23, thereby allowing airflow 31 to flow unrestrictedly in one direction, from the outside, into the mask. If the system does not include the valve 26, the air from the outside atmosphere flows into the mask through the valve 27.

The air flow 32 through the valve 27 may be bi-directional and is controllable by the controller 73. The valve 27 is normally open and is controllable to be completely open, completely closed or partially open, thus controllably restricting the airflow. During expiration, the air exhaled by the patient flows out through the valve 27. When the airflow through the valve 27 is restricted by completely or partially closed valve 27, the air pressure P1 in the mask 23 increases. Therefore, controllably restricting the airflow through the valve 27, allows controlling the pressure P1.

If the sensor 42 is as a pressure sensor, it may be used for a closed loop feedback of the pressure P1 allowing accurate control of the pressure P1 during the TEP period.

Reference is now made back to FIG. 2C which schematically illustrates the air pressure P1 waveform in the mask 23 according to one embodiment of present invention. During the inspiration phase, the pressure in the mask may become negative, causing the valve 26 to open and allowing non restricted airflow into the mask 23 through the valve 26 and preferably through the valve 27. If the valve 26 is not present, the air from the outside atmosphere flows into the mask through the valve 27.

During the expiration phase, the time point T1 is set relative to one or several characteristic reference points in the breathing signal curve as measured by the sensor 42. For example, the time point T1 may be set as a time period relative to the beginning of expiration phase or relative to the time point of the Pmax. The time point T1 may also be set when the pressure P1 reaches a predetermined value Pon, which may be a constant or a may be a value relative to Pmax. For example, T1 may be defined at the time when after the Pmax, P1 decreases to Pon=Pmax*0.8.

At time T1, the controller 73 causes the valve 27 to start restricting the flow, thus causing the pressure P1 to reach a desired value Pb. The valve 27 continues to restrict the airflow until the time point T2.

The time point T2 may be set relative to one or several characteristic reference point in the breathing signal curve as measured by the sensing means 42. For example, the time point T2 may be set as a time period relative to T1. The time point T2 may also be set when the pressure P1 reaches a predetermined value Poff, which may be a constant or a may be a value relative to Pb. For example, T2 may be defined at the time when P1 decreases to Poff=Pb*0.2. or pressure P1 drops to zero.

The values T1, T2, Pon, Pb and Poff are selected such that at the time point T1, the expiration flow and the remaining tidal volume are sufficient to generate the TEP necessary to cause the increase the airway caliber to the extend that prevents or minimizes the frequency of occlusion during the following inspiration phase with minimum expiration discomfort for the patient.

The optimal values of T1, T2, the intensity of flow restriction and the resulting Pb are individual for every patient. Moreover, for the same patient, the optimal parameters may vary from night to night and even during the night.

Typically, the TEP is controlled such that the upper airway occlusion is prevented by automatically and dynamically matching the values Pb, T1 and T2 to the needs of each individual patient, thus preventing occlusion of the upper airway while allowing minimum discomfort in expiration. Typically, in normal breathing, the exhalation airflow is the highest at the beginning of the expiration phase. Therefore, the earlier in the expiration phase the flow restriction starts, the higher may be the pressure Pb. The Pb may also be controlled by the level or intensity of flow restriction (to what extent the valve 27 is closed) and the duration (T2-T1) of the restriction period.

The parameters T1, T2 and Pb may be dynamically adjusted during the treatment using a predetermined algorithm. For example, by manipulating the T1, T2 and the intensity of flow restriction of the valve 27, the pressure Pb may be gradually increased in each subsequent breath cycle, until reaching an optimal value of Pb (Optimal Pb) at which the frequency of apnea events is minimal. In a similar manner, the algorithm may gradually modify the onset (T1) and duration (T2-T1) of the TEP until optimal parameters for the individual patient are reached. Moreover, manipulating the intensity of restriction allows controlling the shape of pressure P1 curve during the TEP, which may allow further optimization of treatment.

For example, the TEP may be set to overlap with the Expiration Ending Segment as illustrated in FIG. 2C. The T1 may be set when a declining P1 reaches the value P1=Pon as detected by the sensor 42. At that point, the controller 73 causes the valve 27 to partially or completely close. Consequently, the airflow through the valve 27 is substantially reduced and the air pressure P1 in the mask rises to the Pb value. After the pressure P1 reaches the Pb value, the controller 73 may keep the valve 27 partially closed, thus allowing a slow reduction in pressure P1 until the onset of the following inspiration phase. The T2 may be set at P1=Poff=0. At that point, the controller 73 causes the valve 27 to completely open to allow the airflow into the mask 23.

The pressure P1 falling below zero is indicative of the beginning of the inspiration phase. Throughout this specification the reference to negative pressure is intended to incorporate a reference to pressure below the atmospheric pressure while a zero pressure is intended to incorporate a reference to the atmospheric pressure.

Figure 4:
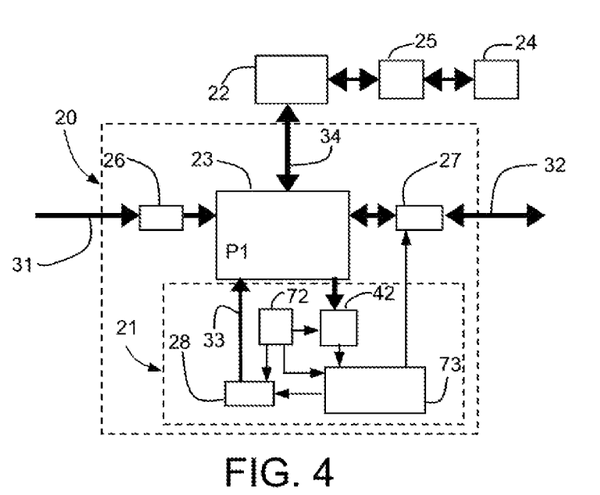
FIG. 4 is a schematic diagram of another embodiment incorporating the principles of present invention.

Reference is now made to FIG. 4 that illustrates an example of the apparatus 20, in which the pressure generator unit 21 further includes a pressure surge generator 28 capable of producing a surge of pressurized air within the mask 23. Throughout this specification the reference to "pressure surge generator" is intended to incorporate a reference to a miniature device capable of providing a short surge of highly pressurized air.

The pressure surge generator 28 is controllable by the controller 73, and is sealably connected to the mask 23. When activated, the pressure surge generator 28 produces the TEP by injecting a surge of pressurized air 33 into the mask 23. If at that time the occlusion in the upper airway is present, and the valve 27 is substantially closed, such surge of pressurized air causes a temporary elevated pressure in patient's upper airway above the occlusion.

Figure 5:
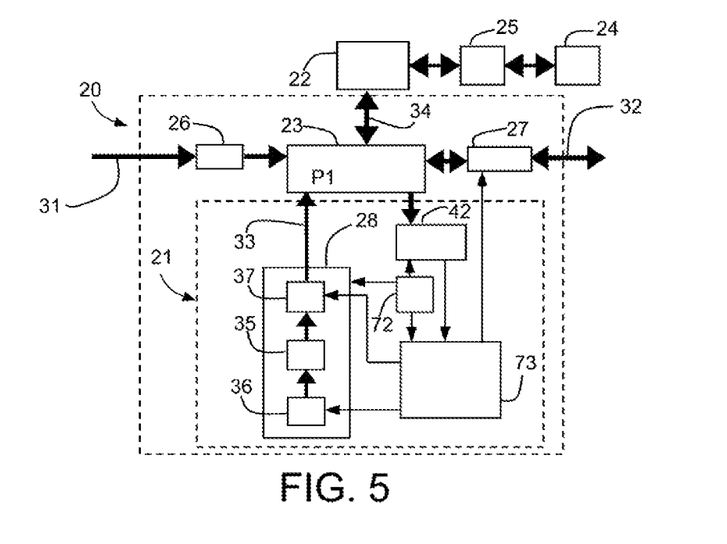
FIG. 5 is a more detailed schematic diagram of the embodiment of FIG. 4.

In the example apparatus shown in FIG. 5, the pressure surge generator 28 consists of an air pump 36 capable of generating pressurized air. The pump 36 may be a miniature device capable of generating air pressure. As opposed to blowers, turbines, fans and alike that are relatively large, heavy and noisy but capable of producing high flow of air (tens of l/m), the pump 36 may be small size and light weight (approximately 10-20 gr.) Typically, the pump 36 has low power consumption and may be capable of generating air pressure of several hundred mbar, while producing airflow of several hundreds ml/min. The pressure surge generator 28 further consists of a pressurized gas storage element 35 capable of accumulating and/or storing the pressurized air (the pressurized gas storage element is described in greater details below). The volume of the air in the pressurized gas storage element 35 may be relatively small, preferably between several tens and several hundred milliliters. That allows making the size of the pressure surge generator 28 very small and light weight. The air in the pressurized gas storage element may be pressurized by the pump 36 to a pressure level of several hundred mbar.

The pressure surge generator 28 further includes a controllable, normally closed valve 37. When the valve 37 is set open by the controller 73, the pressurized air from the pressurized gas storage element 35 is rapidly released into the mask 23, thus elevating the pressure P1 in the mask 23 above the level sufficient to remove the occlusion in the upper airway. Alternatively, the airflow from the pump 36 may flow into the mask through the valve 37 bypassing the pressurized gas storage element 35. Both the pump 36 and the valve 37 are controlled by the controller 73.

Figure 2E:
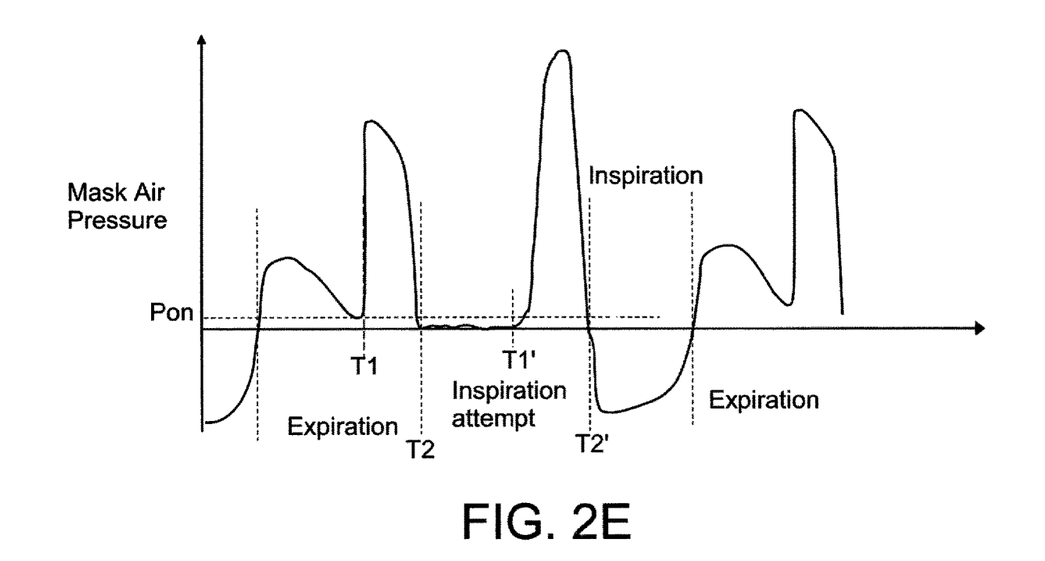
FIG. 2E is an illustration of a pressure waveform within subject's mask operational according to the principles of present invention when an occlusion in the upper airway occurs.

FIG. 2E illustrates an example of a typical pressure waveform in the mask 23. In this example, the upper airway becomes occluded so the inspiration phase does not start normally within a pre-selected period of time Td after the end of the expiration period as detected by the sensing means 42. Consequently, the controller 73 completely closes the valve 27 (at time point T1'), thus creating a sealed chamber consisting of a portion of the patient's upper airway above the occlusion and the mask 23. The controller 73 then activates the pressure surge generator 28 thus proving a surge of pressurizes air from the pressurized gas storage element 35 into the mask 23. Consequently, the pressure P1 in the mask 23 rises, as well as the pressure in the patient's upper airway above the occlusion, until the occlusion is removed.

The removal of occlusion produces airflow along the pharyngeal sensors, which in turn may trigger the pharyngeal dilator reflex. The reflex should activate the pharyngeal dilator muscles that keeps the upper airway from collapsing as long as the negative pressure and the airflow created by inspiration persist. Typically, the time duration Td is selected to be several seconds, but preferably such that allows restoring the patency of the upper airway in less than 10 seconds or in less than any minimum period of time that may be considered an apnea event in the medical literature.

When the occlusion is removed, the pressure P1 drops below zero (time point T2'). At that point the valve 26 (in the embodiment where the valve 26 is present) opens, allowing atmospheric airflow into the mask. Additionally, the controller 73 may open the valve 27 to allow and/or further increase the airflow into the mask 23. If the system does not include the valve 26, the air from the outside atmosphere may flow into the mask through the valve 27.

The pressurized air may also be provided at the end of the EES, regardless the occlusion of the upper airway. If no occlusion is present, the pressurized air may flow into the lungs without causing any inconvenience to the patient.

The Mask

The mask 23 may be a nasal only or a "full face" mask covering both the nostrils and the mouth. Reference is now made to one embodiment shown in FIG. 6A, which illustrates a detailed cross-sectional view of a nasal mask 123. The mask 123 may be an example of the mask 23 referred to above. The mask 123 comprises a housing 113 made of rigid or semi-rigid polymer or elastomer materials such as silicone rubber. The mask 123 further comprises a nozzle assembly 122 made of silicone or similar material. The nozzle assembly 122 is permanently or removably connected and sealed to the housing 113, allowing openings 124 between the nozzle 122 and the housing 113. The housing further comprises an opening 212 and an optional opening 214.

Figure 6A:
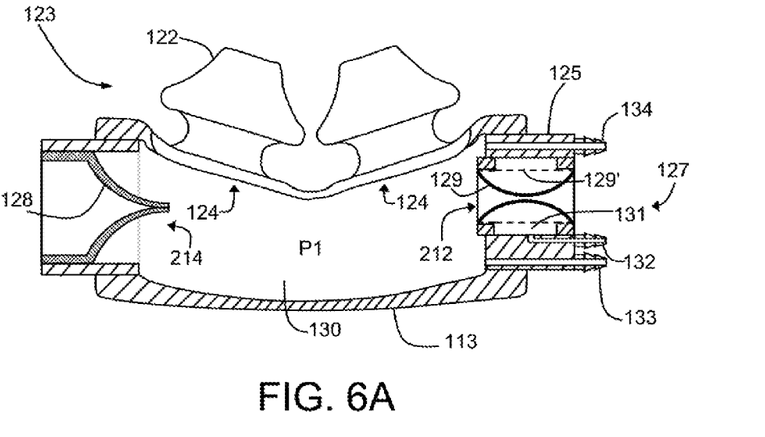
FIG. 6A illustrates a detailed description of a mask according to one embodiment of present invention.

The housing 113 may further comprise of a one-directional valve 128 sealingly installed in the opening 214. The valve 128 may have any suitable design known in the art. An example of such valve is Duckbill valve made by Vernay Laboratories, Inc. (Ohio, USA).

Controllable Breathing Valve

The housing 113 further comprises a breathing valve 127 sealingly and preferably removably installed in the opening 212. The valve 127 comprises a housing 125 that may be made of rigid or semi-rigid plastic material. The valve assembly 127 may further comprise a thin wall, elastic tube 129, sealingly installed inside the housing 125 and forming a vent connecting the volume 130 within the mask 123 with the outside atmosphere. The valve 127 further comprises a sealed chamber 131 between the housing 125 and the outside wall of the tube 129 illustrated by a dashed line. The chamber 131 has an opening port 132 through which pressurized air may be provided into the camber 131 causing the tube 129 to collapse or to bulge inwards thus restricting the airflow through valve 127. The restriction may be partial or complete closure of the valve 127. The degree of restriction is be controlled by providing pressurized air to the port 137 for a predetermined period of time.

The pressure inside the chamber 131 may be made high enough to overcome the pressure difference between the pressure P1 and the atmospheric pressure outside the mask, thus keeping the valve 127 closed. When the pressure in chamber 131 is released, through port 132, the wall of tube 129 returns to its previous shape 129' to allow non-restricted air flow through the valve 127. The pressure in the chamber 131 may be set to make the valve completely open or completely closed or partially open, thus controlling the pressure P1 within the mask 123.

Figure 6B:
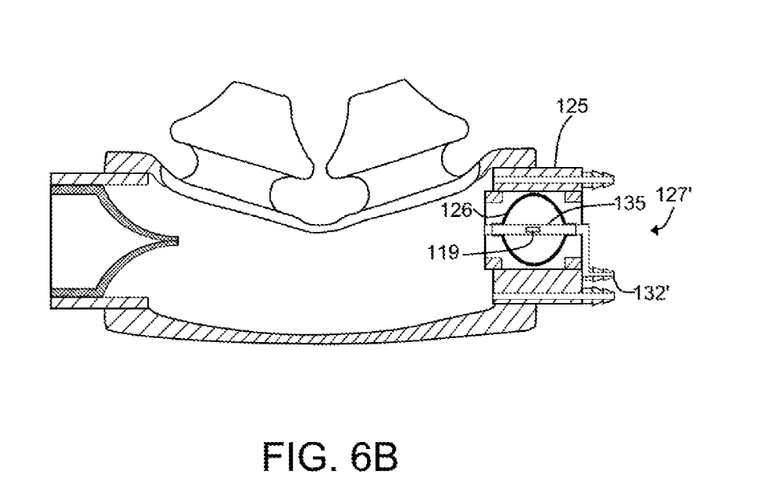
FIG. 6B illustrates a detailed description of a mask with an alternative design.

FIG. 6B illustrates a valve 127' that has alternative design to the valve 127. Instead of the collapsible tube 129, the valve 127' comprises of small diameter inner tube 135 disposed co-centrally in the housing 125. The distal end of the tube 135 is sealed, while the proximal end of tube 135 is connected to an opening port 132' through which pressurized air may be provided. The distal and the proximal ends of the inner tube 135 are fixed to the housing 125 with plurality of spokes that allow substantially non restricted passage of air though the valve 127'. The inner tube has an air passage opening 119 that connects the lumen of the inner tube 135 to the inside wall of a balloon 126 that is disposed on top of the inner tube 135 with proximal and distal ends of the balloon sealingly connected to the inner tube 135. A pressurized air is provided to the port 137', causing the balloon 126 to inflate and to restrict the airflow through the valve 135. The degree of restriction may be controlled by providing the pressurized air to the port 137' for a predetermined period of time.

When the valve 127 is completely open, the opening is large enough to allow sufficient, non restricted flow during spontaneous breathing. The cross section area of the valve 127 vent in its complete open state is preferably be at least approximately 0.2 cm2 but preferable approximately 0.5 cm2 or higher.

It should be noted that providing pressurized to port 132 may be accomplished in different ways. One way of providing the pressurized air may be from the pressurized air generator as described below. Alternatively, the port 132 may receive pressurized air or other gas from a small canister (not shown).

Instead of the valve assembly 126, the opening 214 may be sealed. In yet another embodiment, the valve 126 is replaced by another valve (not shown) that is similar to the valve 127 and that may be utilized simultaneously and in parallel with the valve 127.

The housing 125 further comprises an opening port 133 for pneumatically connecting the volume 130 to the sensing means 42.

The housing 125 further comprise an opening port 134 for providing pressurized air from the pressure generator 21 into the mask 123.

The Pressurized Gas Storage Element

Figure 7A:
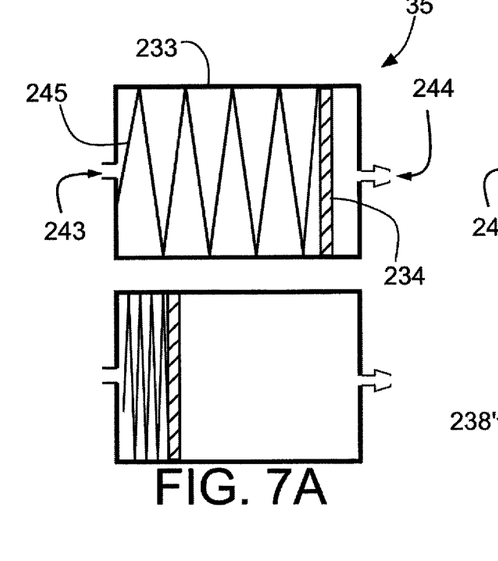
FIG. 7A illustrates an example of a pressurized gas storage element.

Reference is now made FIG. 7A illustrating in details a cross section view of one embodiment of a pressurized gas storage element 35. The pressurized gas storage element 35 comprises of a barrel 233, made of rigid plastic that has an opening 243 in one side and an opening 244 in the second side. The pressurized gas storage element 35 further comprises a plunger tip 234, made of rubber or similar material and is adapted to sealingly slide within the barrel (like in a syringe). The pressurized gas storage element 35 may comprises a spring 245 that is situated between the opening 243 of the barrel 233 and the plunger tip 234. If pressurized air is presented to the opening 244, the plunger tip 234 slides within the barrel towards its closed end, thus loading the spring 245.

Figure 7B:
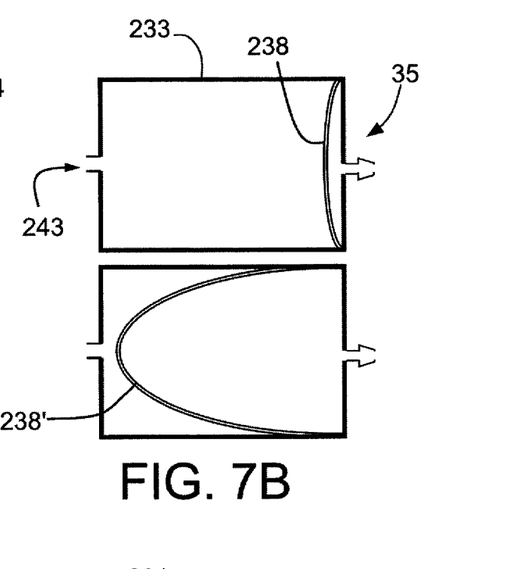
FIG. 7B illustrates another example of a pressurized gas storage element.

Reference is now made to FIG. 7B illustrating in details a cross section view of another pressurized gas storage element 35. In this embodiment, an elastic membrane 238 is used instead of the plunger tip 234 and the spring 245 of FIG. 7A. If pressurized air is presented to the opening 244, the pressure difference causes the membrane 238 to stretch within the barrel and to capture the pressurized air in the created volume.

Yet another variation of the pressurized gas storage element 35 may be a balloon made of elastic material such as natural or synthetic rubber.

It must be noted that the pressurized gas storage element may have other embodiments. In those embodiments the pressurized gas storage elements, when discarded, the air may be released not only due to pressure difference, but also by the elastic power of the pressurized gas storage element's structure. This may allow maintaining the high pressure in the pressurized gas storage element until substantially all the air is discharged. The spring 245 or the elastic membrane/balloon may be selected such that the pressure required to fill the pressurized gas storage element may be between 20 and 1000 cmH2O, but preferably between 200 and 500 cmH2O.

The pressurized gas storage element 35 may also be made of rigid container, such as a gas cylinder, that may discharge pressurized air until pressure equilibrium is reached.

The Pressure Generator Unit

Figure 8:
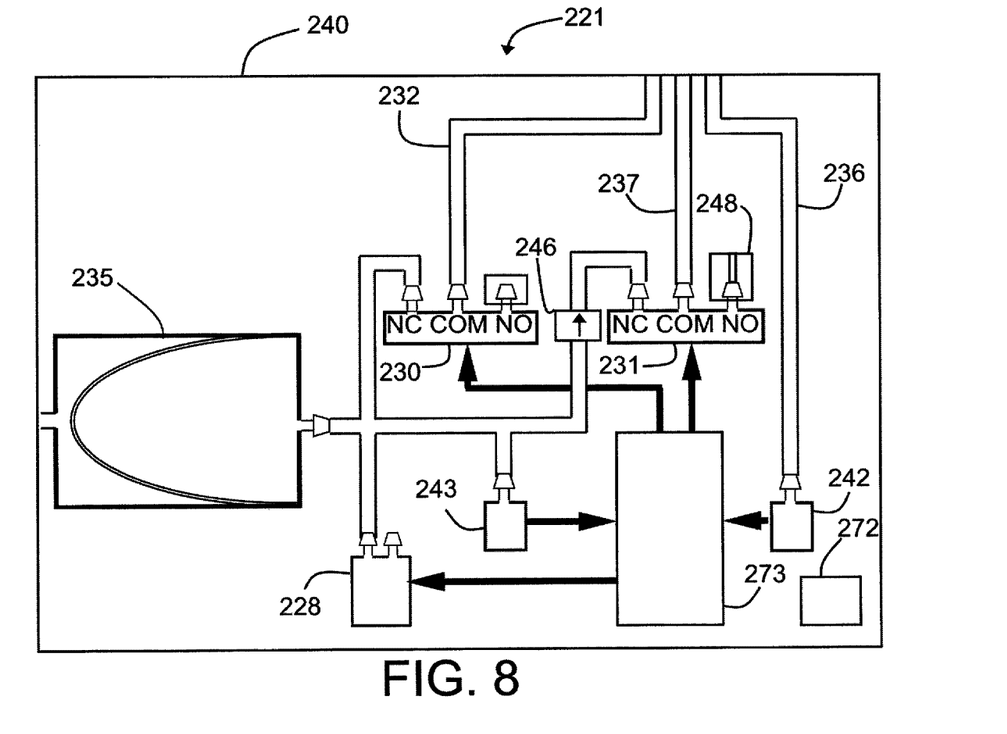
FIG. 8 illustrates a detailed description of a pressure generator unit according to one embodiment of present invention.

FIG. 8 is a detailed description of a pressure generator unit 21. In the illustrated embodiment, the pressure generator unit 221 comprises a miniature air pump 228 serving as pressure generator 36 of FIG. 5. An example of such air pump is 228 is a diaphragm pump 2002 VD DC manufactured by Gadner Denver Thomas Gmbh (Pucheim, Germany). The pump is controlled by a controller 273 that is capable of providing sufficient current to drive the pump at variable pumping speed and switching the current on and off. The pump 228 is pneumatically connected to a pressurized gas storage element 235 similar to the pressurized gas storage element 35 described in FIG. 7B. The pump 228 and the pressurized gas storage element 235 are pneumatically connected to a pressure sensor 243, which is electrically connected to the controller 273 for controlling the pressure in the pressurized gas storage element 235. An example of such pressure sensor is MPX5010 manufactured by Freescale Semiconductor, Inc. (Arizona, USA).

The pressurized gas storage element 235 is pneumatically connected to a normally closed (NC) port of a valve 230. The valve 230 may be a 3 ways, 2 positions, miniature solenoid valve, such as the PDS-50 manufactured by the LEE Company Inc (CT, USA). The common port (COM) of the valve 230 is pneumatically connected to the port 134 of the mask 123 through a tube 232 made of flexible material such as silicone. The normally open port NO of the valve 230 is sealed. The switching between the positions of valve 230 is controllable by the controller 273.

The pressurized gas storage element 235 is pneumatically connected to a normally closed (NC) port of a valve 231 through a one-way check valve 246. The valve 246 is positioned to allow air flow from the pressurized gas storage element 235 to the valve 231. An example of such check valve is the X-30465 manufactured by Vernay Labs (OH, USA). The valve 231 may be similar to the valve 230. The common port (COM) of the valve 231 is pneumatically connected to the port 132 of the mask 123 through a small tube 237 made of flexible material such as silicone. The normally open port NO of the valve 231 is open to the atmosphere directly or through a flow reducer 248. The switching between the positions of valve 231 is controllable by the controller 273.

The pressure generator unit 221 furthers comprise a pressure sensor 242. An example of such pressure sensor is the 5701 Low Pressure Module manufactured by Measurement Specialties, Inc. (VA, USA). The pressure sensor 242 is pneumatically connected to the port 133 of the mask 123 through a small tube 236 made of flexible material such as silicone. The pressure sensor 242 is electrically connected to the controller 273 for providing pressure data within the mask 123.

The pressure generator unit 221 further comprises a power source 272 such as a rechargeable battery. An example of such battery is 56493 Rechargeable Lithium Polymer battery manufactured by VARTA Microbattery (Ellwangen, Germany). The pressure generator unit 221 may further comprise a charging port (not shown) for recharging the power source 272. The pressure generator unit 221 further comprises of a housing 240, typically made of a rigid or semi rigid plastic material.

Typically, the pressure generator unit 221 is operational in the following manner. Preferably, the pump 228 is configured to pumping air into the pressurized gas storage element 235. The pressure sensor 243 continuously monitors the pressure in the pressurized gas storage element 235 keeping it within desired pressure range. Such pressure range may be 20-1000 cmH2O, but more preferably 200-500 cmH2O. The controller 273 controls the pressure by periodically activating the pump 228. The controller 273 may continuously receive the pressure data within the mask from the pressure sensor 242. At the time the valve 127 (FIG. 6A) or the valve 127' (FIG. 6B) needs to be partially or completely closed, the controller 273 activates the valve 231, so the pressurized air is flowing through the tube 237 and causing the tube 129 (FIG. 6A) to collapse or bulge inwards, consequently reducing the cross section area of the vent of the valve 127. In a similar manner, when the valve 127' (FIG. 6B) needs to be partially or completely closed, the controller 273 activates the valve 231, so the pressurized air is flowing through the tube 237 and causing the tube 129' (FIG. 6B) to bulge outwards, consequently reducing the cross section area of the vent of the valve 127'.

The valve 246 prevents a backflow from the chamber 131 (FIG. 6A) if the pressure in the pressurized gas storage element 235 drops. When the valve 127 needs to be opened, the controller 273 deactivates the valve 231, so the pressurized air from chamber 131 escapes through the NO port of the valve 231 to the atmosphere through a flow reducer 248. For example, the flow reducer 248 may allow substantially all the pressurized from the chamber 131 to escape within less than one second.

Sequentially activating and deactivating the valve 231 with a predetermined duty cycle may control the cross section area of the valve 127 and consequently the level of restriction of the valve 127/127' at the required level.

At the time when pressurized air needs to be provided into the mask 123, the controller 273 is activating the valve 231 to close the breathing valve 127/127' and then activating the valve 230, thus causing the pressurized air to flow from the pressurized gas storage element 235 into the mask 123.

Figure 9:
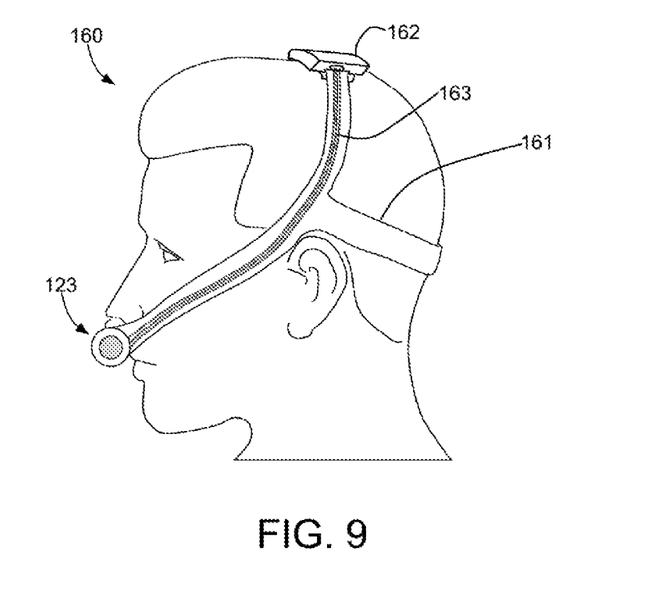
FIG. 9 is an illustration of an example of a system incorporating the principles of the invention applied to the patient.

FIG. 9 illustrates an example of a nasal system 160 that comprises of a mask 123 connected to a headgear 161. The headgear 161 may be made of soft, flexible material adapted to apply the mask 123 sealably and removably to the patient's nostrils. The headgear 161 may further comprise a chinstrap (not shown) that prevents air from leaking out the mouth by holding the chin closed.

The system 160 further comprises a pressure generator unit 162 that may be equivalent to pressure generator unit 221 that may be removably attached to the headgear 161. Instead of being part of the pressure generator unit 162, the pressurized gas storage element 35/235 may be integrated into the headgear 161 in order to minimize the dimensions of the pressure generator unit 162.

The system 160 further comprises a flexible tubing assembly 163 that pneumatically connects the ports 132, 133 and 134 of the mask 123 with the tubes 237, 236 and 232 of the pressure generator unit 221. The unit 221 may further comprise a porting hub (not shown) for quick connection of the tubing assembly 163.

The pressure generator unit 162 may be removably attached to headgear 161 with a snap, e.g., snap-fit, push-pin fit, or stretch-over fit, or equivalent which may allow for simple assembly and disassembly. The pressure generator unit 162 may be constructed as part of the headgear assembly 161 or may be located in any convenient location on the headgear assembly 161. The pressure generator unit 162 may be located outside the headgear assembly 161.

Figure 10:
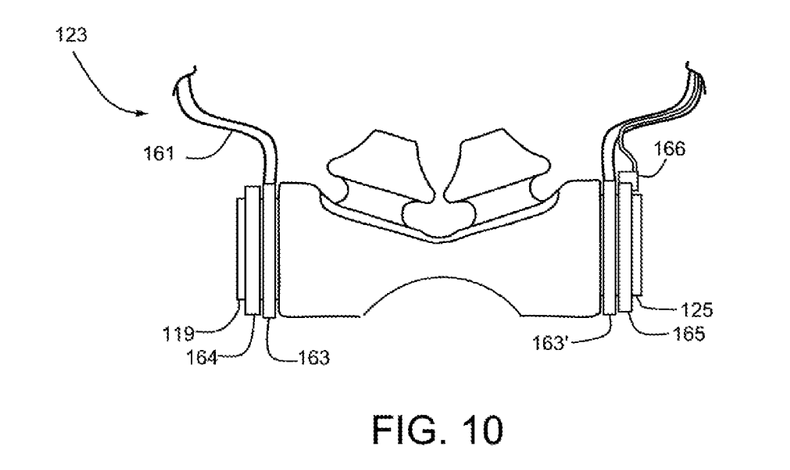
FIG. 10 is an external view of an example of a nasal mask.

As illustrated in FIG. 10, the headgear assembly 161 may further comprise two attachment rings 163 and 163' rotatably and removably attached to the housing 119 and to the housing 125 of the mask 123. The rings 163 and 163' may be made of rigid or semi-rigid elastomer. The headgear assembly 160 may further comprise fastening rings 164 and 165 for securing the rings 163 and 163. The fastening ring 165 may comprise a porting hub 166 for quick connection of the tubing assembly 163 to the ports 132, 133 and 134 of the mask 123.

The present invention may be practiced alone or in combination with other modalities that may be used for measuring parameters required for diagnosis of sleep apnea, such as pulse oximeter and/or motion, temperature, flow and other sensors. In such case, the present invention may serve as both diagnostic and therapeutic tool.

The invention claimed is:

1. A system to facilitate breathing of a subject, comprising:
 a mask adapted to be applied to at least one breathing orifice of said subject;
 at least one controllable breathing valve associated with said mask and configured to be connected between the at least one breathing orifice and ambient atmosphere;
 a sensor for monitoring a waveform of at least one of the breathing cycles of the subject;
 a controller receiving an output of said sensor and adapted to control said at least one controllable breathing valve, said controller being configured to close said at least one controllable breathing valve for a time segment of said waveform, in response to detection by said sensor of airway occlusion for a predetermined time, and
 a pressure surge generator sealably connected to said mask, said pressure surge generator being configured to generate a rapid surge of pressurized air in said mask during said time segment until the occlusion is removed, so as to stimulate resumption of spontaneous inspiration so that pressure within said mask drops below zero on resumption of spontaneous inspiration, said time segment terminating no later than the time when the pressure in said mask drops below zero.

2. The system according to claim 1, wherein said controller is adapted to activate said at least one controllable breathing valve by means of pressurized gas, from a completely open state to a completely closed state.

3. The system according to claim 1, wherein said predetermined time is less than 10 seconds.

4. A method to facilitate breathing of a subject, comprising:
 applying a mask to at least one breathing orifice of said subject, at least one controllable breathing valve configured to be disposed between said at least one breathing orifice and ambient atmosphere;
 monitoring a waveform of at least one of the breathing cycles of the subject using a sensor;
 determining the waveform indicates airway occlusion for longer than a predetermined time, and subsequently:
  activating closing of a flow through said at least one controllable breathing valve for a time segment of said waveform; and
  generating a rapid surge of pressurized air in said mask during said time segment, by means of a pressure surge generator sealably connected to said mask, until the occlusion is removed, so as to stimulate resumption of spontaneous inspiration so that pressure within said mask drops below zero on resumption of spontaneous inspiration, said time segment terminating no later than the time when the pressure in said mask drops below zero.

5. The method according to claim 4, wherein said at least one controllable breathing valve is activated by means of pressurized gas from a completely open state to a completely closed state.

6. The method according to claim 4, wherein said predetermined time is less than 10 seconds.

* * * * *